United States Patent
Mihalca et al.

[11] Patent Number: 5,964,696
[45] Date of Patent: Oct. 12, 1999

[54] STEREOSCOPIC IMAGING BY ALTERNATELY BLOCKING LIGHT

[75] Inventors: Gheorghe Mihalca, Chelmsford; Yuri E. Kazakevich, Andover, both of Mass.

[73] Assignee: Smith & Nephew, Inc., Memphis, Tenn.

[21] Appl. No.: 08/740,206

[22] Filed: Oct. 24, 1996

[51] Int. Cl.[6] ........................................... A61B 1/04
[52] U.S. Cl. .................. 600/166; 600/111; 348/45
[58] Field of Search ..................... 600/111, 166, 600/173, 181; 348/45, 57, 58; 359/376, 464, 465

[56] References Cited

U.S. PATENT DOCUMENTS

| | | |
|---|---|---|
| 4,884,876 | 12/1989 | Lipton et al. . |
| 4,924,853 | 5/1990 | Jones, Jr. et al. ........................ 600/111 |
| 5,222,477 | 6/1993 | Lia . |
| 5,385,138 | 1/1995 | Berry ...................................... 600/166 |
| 5,588,948 | 12/1996 | Takahashi et al. . |
| 5,613,936 | 3/1997 | Czarnek et al. ......................... 600/166 |
| 5,649,897 | 7/1997 | Nakamura et al. ...................... 600/111 |
| 5,743,846 | 4/1998 | Takahashi et al. ...................... 600/166 |
| 5,743,847 | 4/1998 | Nakamura et al. ...................... 600/166 |

FOREIGN PATENT DOCUMENTS

| | | |
|---|---|---|
| 9308618 | 11/1993 | Germany . |
| WO 95/28662 | 10/1992 | WIPO . |

OTHER PUBLICATIONS

Francis A. Genkins et al., Fundamentals of Optics, McGraw Hill, pp. 116–120 (1976).

"Polarization control with polymers and liquid crystals," Meadowlark Optics, Brochure (1995).

Thomas N. Mitchell, "Three–dimensional endoscopic imaging for minimal access surgery," J.R. Coll. Surg. Edinb., Oct. 1993, pp. 285–292.

W.P. Griffin, MSEE, MSCP, "Three–Dimensional Imaging In Endoscopic Surgery," Biomedical Instr. & Technology, May/Jun. 1995, pp. 183–189.

"Achromatic Rotator," Displaytech, Inc., Product Brochure, 2 pages (Apr. 1996).

*Primary Examiner*—John P. Leubecker
*Attorney, Agent, or Firm*—Fish & Richardson P.C.

[57] ABSTRACT

A stereoscopic imaging device is described that attaches to an instrument, such as an endoscope or a borescope, which is characterized by an exit pupil in the vicinity of its proximal region. The imaging device includes a dual aperture plate and an optical switch that are disposed within a housing that attaches to the proximal region of the instrument. The dual aperture plate defines right and left, spaced-apart apertures respectively disposed at symmetric locations substantially in the plane of the exit pupil of the instrument. The optical switch alternately blocks light received from the instrument and passing through the right and left optical channels so that a stereoscopic view can be generated.

33 Claims, 5 Drawing Sheets

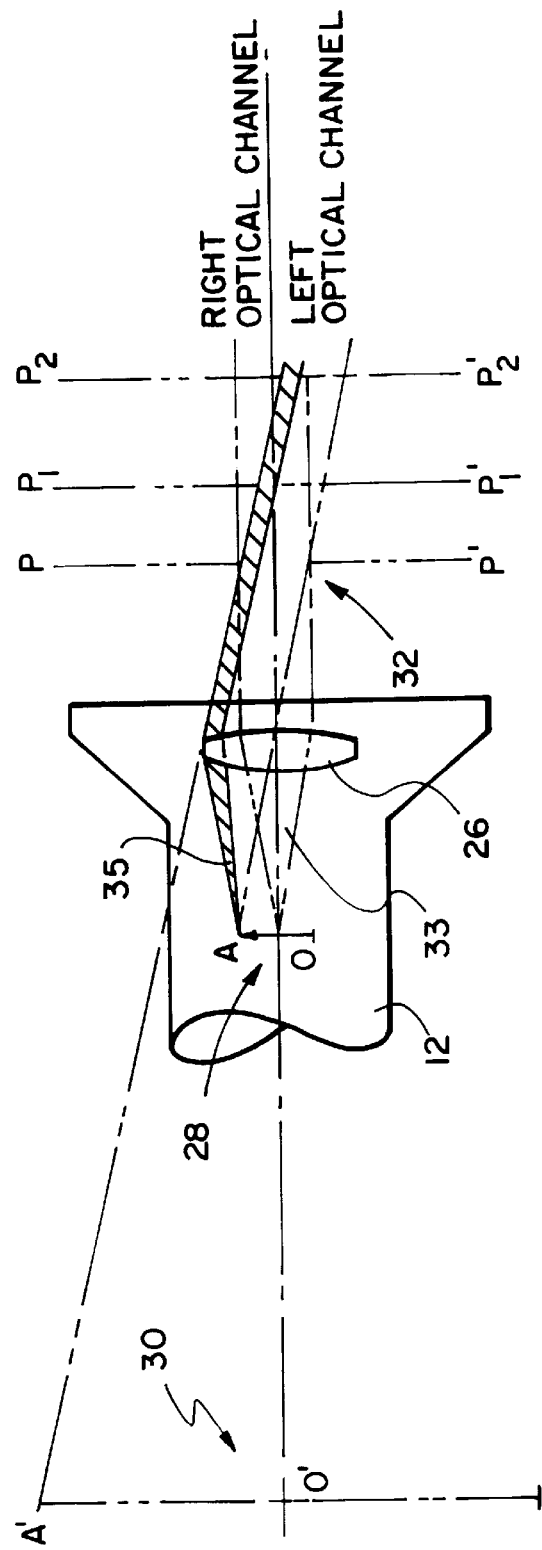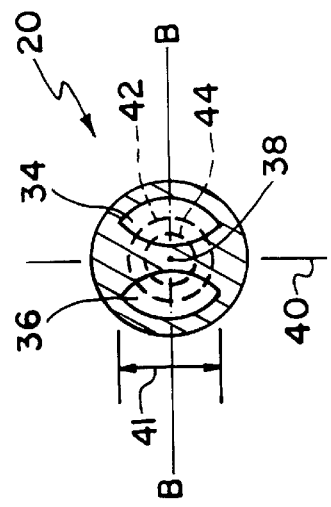
FIG. 2A
FIG. 3

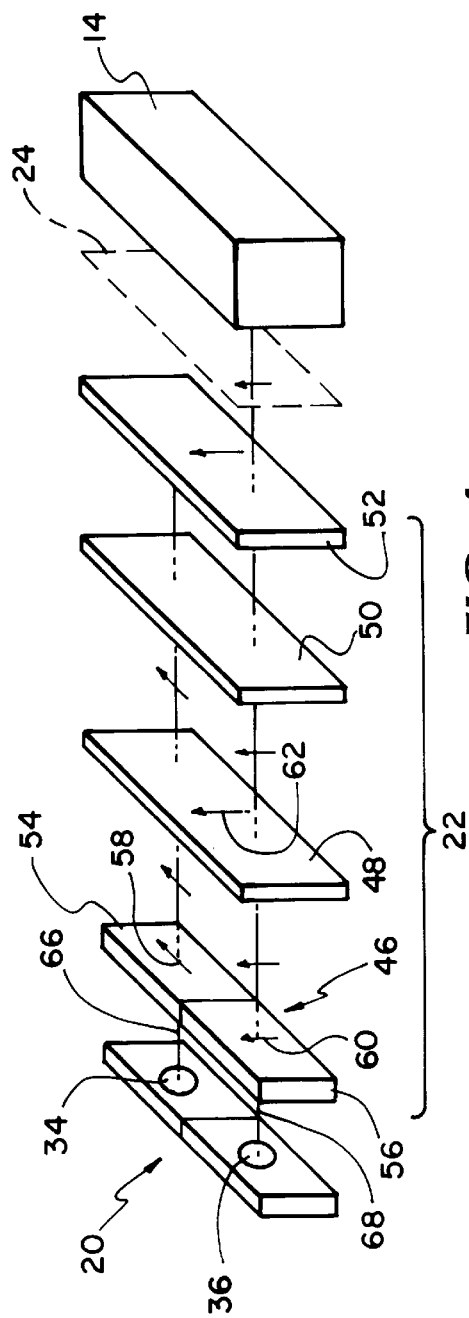
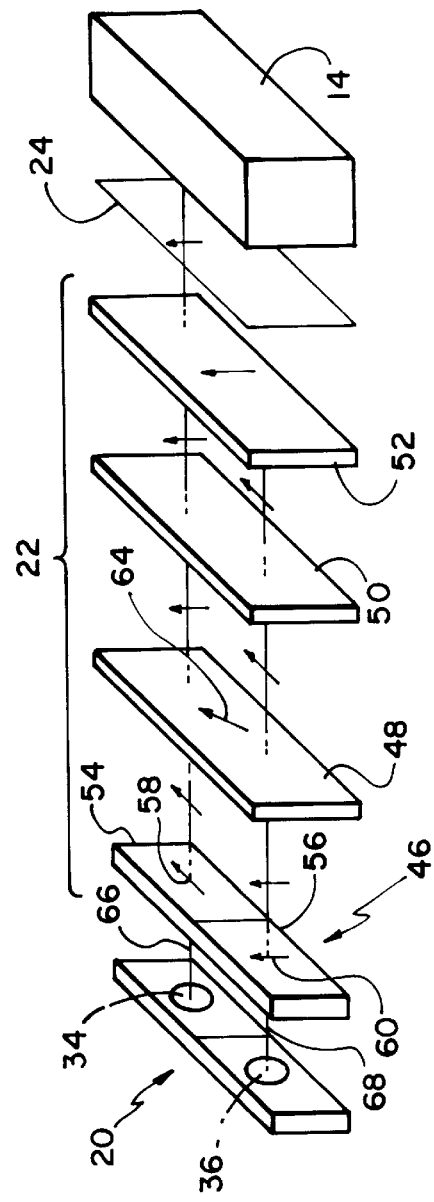
FIG. 4
FIG. 4A

STEREOSCOPIC IMAGING BY ALTERNATELY BLOCKING LIGHT

BACKGROUND OF THE INVENTION

This invention relates to stereoscopic imaging systems and methods for instruments, such as endoscopes, borescopes, and the like.

Stereoscopic imaging of an object is achieved by respectively presenting to a viewer's right and left eyes images of the object from different, spatially-separated perspectives. The viewer's brain "fuses" these images into a single image so that the viewer perceives a sense of depth. Most endoscopes present only two-dimensional images to a viewer or to a video camera attached to the proximal end of the endoscope. Stereoscopic imaging systems for endoscopes have, however, been recently proposed. For example, Lia (U.S. Pat. No. 5,222,477) describes an endoscope that incorporates a stereo imaging system at the distal end of the scope. Mitchell et al.("Three-dimensional endoscopic imaging for minimal access surgery," *Journal of the Royal College of Surgeons of Edinburgh,* Vol. 38, No. 5, pp. 285–292 (Oct. 1993)) and Greening et al. (International Publication No. WO 95/28662) describe a stereoscopic imaging system that is mounted on the proximal end of an endoscope to present right and left images of a scene captured by the endoscope to a video camera. Endoscopic stereo systems that capture images of a scene from two different perspectives using two CCDs mounted at the distal end of the scope have also been proposed.

SUMMARY OF THE INVENTION

The invention concerns a stereoscopic imaging system for attachment to an instrument, such as an endoscope or a borescope, which is constructed to transmit light from a distal region of the instrument to a proximal region of the instrument and is characterized by an exit pupil located in the vicinity of the proximal region of the instrument.

In one aspect, the invention features devices and methods for generating a stereoscopic image that includes receiving light from the instrument, and, at symmetric locations substantially in the plane of the exit pupil of the instrument, defining right and left optical channels, and using an optical switch to alternately block the right and left optical channels for generating a stereoscopic view.

Because the right and left optical channels are defined substantially in the plane of the exit pupil of the instrument, light received from the instrument is divided equally into the right and left channels, whether or not the light is received along the optical axis of the instrument. This reduces leakage (cross-talk) between the right and left channels and enhances the perceived stereoscopic effect. The resulting enhanced depth perception enables a user to readily maneuver an endoscope within a patient's body during a medical procedure, or to readily maneuver a borescope during an industrial process, improving the accuracy of the procedure and reducing the overall time needed to complete the procedure.

In another aspect, the invention features devices and methods for generating a stereoscopic image that includes axially moving a dual aperture device with respect to the proximal end of the instrument to respectively position right and left apertures at symmetric locations substantially in the plane of the exit pupil of the instrument. This feature enables a user to accommodate different instruments by adjusting the dual aperture device so that the right and left apertures are disposed substantially in the plane of the exit pupil, the relative position of which varies for different instruments.

In other aspects, the invention features combinations of the instrument, the stereoscopic imaging device, and a camera.

Embodiments may include one or more of the following.

The optical switch alternately blocks light received from the instrument based on the polarizations of the right and left optical channels. The optical switch comprises a first polarizer for polarizing the right and left optical channels, a second polarizer for permitting light of a selected polarization to pass therethrough, and a polarization rotator disposed between the first and second polarizers for alternately rotating the polarization of the right and left optical channels. The polarization rotator is, e.g., a ferroelectric liquid crystal (FLC) rotator. Such FLC rotators can have switching times on the order of 35–90 $\mu$s. For many video applications, such a high switching speed reduces leakage between the right and left channels—leakage which could degrade the stereoscopic effect.

In some embodiments, the first polarizer polarizes the right and left optical channels with orthogonal polarizations, and the polarization rotator is characterized by a first state wherein the right and left optical channels are not rotated by the polarization rotator and by a second state wherein the right and left optical channels are rotated 90° by the polarization rotator. The first polarizer comprises two separate polarizers with polarization axes oriented at 90° with respect to each other. The first polarizer is disposed adjacent to the dual aperture plate substantially in the plane of the exit pupil of the instrument when the adaptor is attached thereto. An optical retarder is coupled to the housing and disposed between the polarization rotator and the second polarizer for adjusting contrast ratios of the right and left optical channels.

In other embodiments, the first polarizer polarizes the right and left optical channels with the same polarization, and the polarization rotator is characterized by a first state wherein the right optical channel is not rotated by the polarization rotator and the left optical channel is rotated 90° by the polarization rotator, and by a second state wherein the right optical channel is rotated by 90° by the polarization rotator and the left optical channel is not rotated by the polarization rotator. The polarization rotator preferably comprises two separate ferroelectric liquid crystal polarization rotators with optical axes oriented at 45° with respect to each other. The first polarizer and the polarization rotator are disposed adjacent to the dual aperture plate substantially in the plane of the exit pupil of the instrument when the housing is attached thereto.

The right and left apertures of the dual aperture plate may be symmetrically spaced from a common axis, and the right and left apertures may be elongated along a respective dimension parallel to the common axis; for example, the right and left apertures may be generally elliptical in shape. Such a shape improves the tradeoff between stereopsis and light energy throughput for different endoscopes, while accommodating a wide range of exit pupil diameters.

The housing may be adapted to attach to a camera. The imaging device may also comprise an optical system for delivering light from the left and right channels to a single imaging sensor for generating a stereoscopic view. The imaging system may also comprise an optical switch driver which is synchronized with the video imaging system field rate and with the display so that a viewer sees the right optical channel with the right eye and the left optical channel with the left eye.

Other features and advantages will become apparent from the following.

BRIEF DESCRIPTION OF THE DRAWINGS

FIG. 2A is a diagram useful in understanding the stereoscopic imaging device of FIGS. 1 and 2.

FIG. 3 is a sectional view of a dual aperture plate, taken along the line 3—3 in FIG. 2.

FIGS. 4 and 4A are diagrammatic views of an optical switch for different states of operation.

DESCRIPTION OF THE PREFERRED EMBODIMENTS

Figure 1:
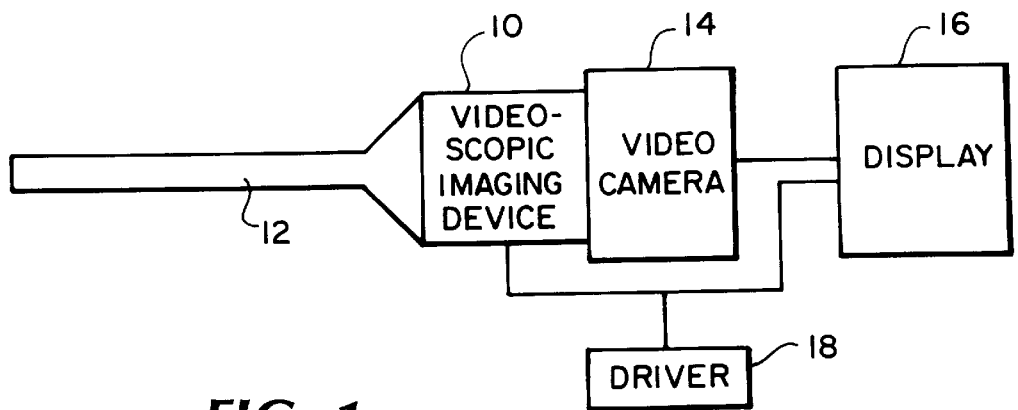
FIG. 1 is a diagrammatic view of a stereoscopic imaging device attached to the proximal end of an endoscope for presenting a stereoscopic view on a display.

Referring to FIG. 1, a stereoscopic imaging device 10 is attached to the proximal end of an endoscope 12. Imaging device 10 alternately produces a right perspective image and a left perspective image of a two-dimensional image captured by the endoscope for generating a stereoscopic view (e.g., a stereoscopic view of a region inside a patient's body). A video camera 14 generates right and left video signals from the right and left images produced by stereoscopic imaging device 10. A display 16 receives the right and left video signals and alternately presents the right and left images to a viewer. A driver 18 coordinates the operation of an optical switch in stereoscopic imaging device 10 with the presentation of the images on display 16. The driver is synchronized with the video imaging system field rate and with the display so that a viewer sees the right optical channel with the right eye and the left optical channel with the left eye. Stereoscopic imaging device 10 can be detached from the proximal end of endoscope 12 to allow the user to directly view the two-dimensional image captured by the scope.

Display 16 presents the right images to one of the viewer's eyes and the left images to the other eye. Display 16 may consist of a standard video monitor which alternately displays the right and left images, and a pair of glasses with liquid crystal shutters that are synchronized with the monitor and alternately block the viewer's right and left eyes. Display 16 may alternatively consist of a video monitor which polarizes the right images differently from the left images, and glasses with circular right and left polarization filters that enable right images to reach one of the viewer's eyes and left images to reach the other eye. The right and left images are presented to the viewer's eyes at a rate that is sufficiently rapid for the viewer's brain to fuse the right and left images into a single image, which the viewer perceives as having sense of depth. Such depth perception enables the viewer to readily maneuver endoscope 12 within a patient's body during an endoscopic procedure, or to readily maneuver a borescope during an industrial process, improving the accuracy of the procedure and reducing the overall time needed to complete the procedure.

Figure 2:
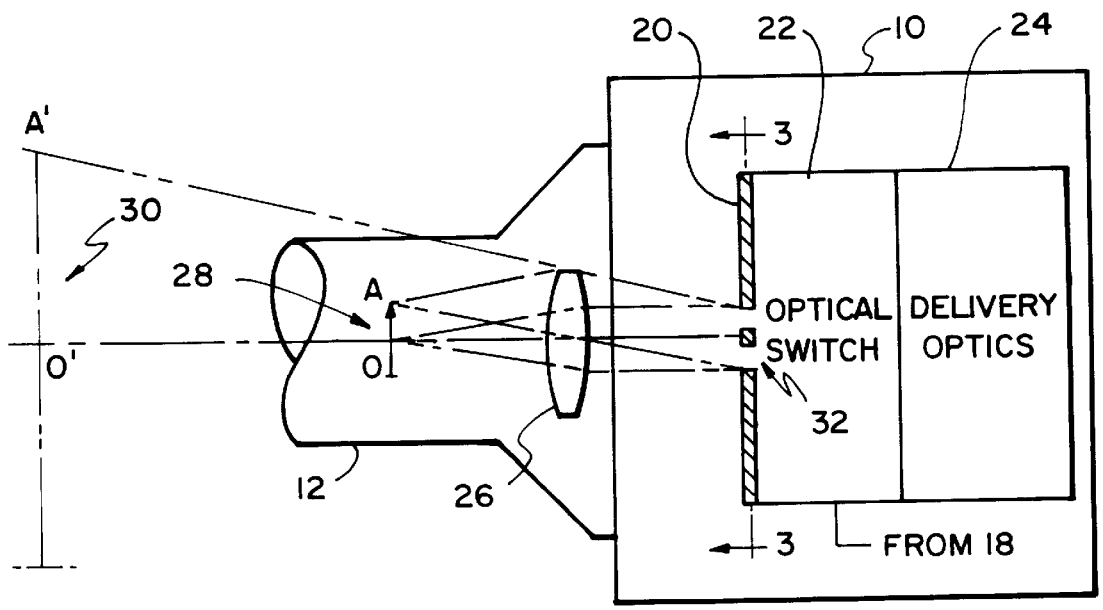
FIG. 2 is a diagrammatic view of the stereoscopic imaging device of FIG. 1 and the proximal end of the endoscope shown in FIG. 1.

As shown in FIG. 2, stereoscopic imaging device 10 includes a dual aperture plate 20, an optical switch 22 that is controlled by driver 18 (FIG. 1), and delivery optics 24 that deliver the images from optical switch 22 to video camera 14. The proximal end of endoscope 12 includes an ocular lens 26 that receives light from the distal end of the endoscope and directs the light onto dual aperture plate 20. Because the field aperture stop of a rigid endoscope (such as endoscope 12) and the proximal fiber face of a flexible endoscope are typically located in the vicinity of the first focal point of ocular lens 26, ocular lens 26 produces a distally-located magnified virtual image 30 (plane A'-O') of the object that can be viewed directly by the viewer in the direct-view application (i.e., with stereoscopic imaging device 10 and videocamera 14 removed).

Endoscope 12 is characterized by an exit pupil 32. Because most endoscopes have a telecentric ray path distally of the ocular lens, exit pupil 32 is located near a second focal point of ocular lens 26. The distance from the proximal end of endoscope 12 to exit pupil 32 is typically referred to as the "eye relief." As described below, aperture plate 20, and one or more components of optical switch 22 are positioned in the plane of exit pupil 32. For this reason, the light received from endoscope 12 is equally divided into right and left optical channels, whether or not the light is received along the optical axis of endoscope 12. If the received light were divided at a location other than at exit pupil 32, off-axis light beams would be unequally divided, reducing the stereoscopic effect perceived by the viewer. Furthermore, the leakage (cross-talk) between the right and left channels increases when the light is divided at locations other than at exit pupil 32, further degrading the perceived stereoscopic effect.

The location and diameter of exit pupil 32 is different for different endoscopes, and may be significantly different for endoscopes of different diameter. To provide stereoscopic imaging for different endoscopes, dual aperture plate 20, along with one or more components of optical switch 22, are axially movable with respect to the proximal end of endoscope 12 so that they can be positioned in the plane of exit pupil 32 of endoscope 12.

As shown in FIG. 2A, the position of dual aperture plate 20, along with one or more components of optical switch 22, significantly affects the division of light between the right and left optical channels. When division plane (position of aperture plate 20, along with one or more components of optical switch 22) is positioned in the exit pupil plane P-P', an axial light beam 33 passing through point O and forming a solid angle which is limited by exit pupil 32, and an off-axis light beam 35 passing through point A and forming a solid angle which is also limited by the exit pupil, are both equally divided along optical axis O'-O into right and left optical channels. When the division plane is displaced from exit pupil plane P-P' to plane $P_1$-$P_1$', axial light beam 33 is equally divided into right and left optical channels; off-axis light beam 35, however, is unequally divided into the right optical channel (shown by cross-hatching) and the left optical channel (the unhatched portion of light beam 35). When the division plane is displaced a greater distance from exit pupil plane P-P' to plane $P_2$-$P_2$', the right portion of off-axis light beam 35 becomes completely vignetted. Thus, when the division plane is displaced from exit pupil plane P-P', off-axis light beams will produce greater left channel signals than right channel signals, resulting in greater leakage between the channels and decreasing the perceived three-dimensional effect.

Referring to FIG. 3, dual aperture plate 20 includes right and left apertures 34, 36, respectively, which are symmetrically spaced from a point 38 on a common axis 40 in the plane of plate 20. Apertures 34, 36 are spaced-apart to increase the stereoscopic effect. The shape of apertures 34, 36 is selected to improve the tradeoff between stereopsis and light energy throughput for different endoscopes, while accommodating a wide range of exit pupil diameters. In a preferred embodiment, apertures 34, 36 are generally elliptical in shape (e.g., an ellipse, or in the shape of a trapezoid or a sector of a circle or ellipse) with an elongated dimension 41 that is parallel to common axis 40. Each aperture 34, 36 is preferably symmetrical about axis B—B, which is orthogonal to common axis 40 in the plane of plate 20. By way of example, the projections of exit pupils for different diameter endoscopes are shown in shadow as 42, 44.

Referring to FIGS. 4 and 4A, optical switch 22 includes a polarizer 46, a polarization rotator 48, a polymer retarder 50, and a polarizer 52. Polarizer 46 includes two separate polarizers 54, 56 with polarization axes 58, 60 oriented at 90° with respect to each other. Polarizer 46 is preferably positioned adjacent to dual aperture plate 20 substantially in the plane of exit pupil 32 of endoscope 12, either distally of aperture plate 20 or proximally of aperture plate 20 as shown. The other components (rotator 48, retarder 50, and polarizer 52) can be positioned anywhere in the optical path between polarizer 46 and video camera 14. Preferably, these components are stacked adjacent to polarizer 46.

Polarization rotator 48 is a ferroelectric liquid crystal (FLC) that functions as a broadband switchable half-wave retarder (e.g., an Achromatic Rotator available from Displaytech, Inc. of Boulder, Colo., U.S.A.). Rotator 48 is constructed to rotate the linear polarization of the incoming light by approximately twice the angle the incoming linear polarization makes with the rotator axis. Rotator 48 is switchable between a state (FIG. 4) with an optical axis 62, and a state (FIG. 4A) with an optical axis 64 oriented at an angle of 45° with respect to optical axis 62.

In operation, apertures 34, 36 divide light received from endoscope 12 into right and left channels 66, 68, and polarizers 54, 56 polarize the right and left channels with horizontal and vertical polarizations, respectively. Driver 18 generates a voltage which changes the direction of the liquid crystal polarization rotator optical axis; in the case of the ferroelectric liquid crystal polarization rotator, the voltage generated by driver 18 is ±5 volts. In the first state (FIG. 4), the polarization of right optical channel 66 is orthogonal to rotator optical axis 62; rotator 48 therefore does not rotate the right channel polarization. The polarization of left channel 68 is parallel to rotator optical axis 62; therefore, rotator 48 also does not rotate the left channel polarization. Because the polarization of polarizer 56 is parallel to the polarization of polarizer 52, the contrast of left channel 68 is less than the contrast of right channel 66, which has a polarization that is orthogonal to the polarization of polarizer 52. Polymer retarder 50 rotates the polarizations of right and left channels 66, 68 to enhance the contrast of left channel 68 at the expense of the right channel contrast so that the contrast in right and left channels 66, 68 are substantially the same, with contrast ratios of, e.g., 80:1 to 100:1. Polarizer 52 transmits light with vertical polarization (left channel 68) and blocks light with horizontal polarization (right channel 66). Thus, when polarization rotator 48 is in the first state, video camera 14 receives light only from left channel 68.

In the second state (FIG. 4A), the polarization of right and left optical channels 66, 68 are both oriented at 45° with respect to rotator optical axis 64 and, therefore, rotator 46 rotates the polarization of both the right and left channels by 90°. This results in the polarization of right channel 66 being oriented vertically, and the polarization of left channel 68 being oriented horizontally, causing polarizer 52 to pass right channel 66 and block left channel 68. Thus, when the polarization rotator is in the second state, video camera 14 receives light only from the right channel.

Other embodiments are within the scope of the claims.

Figure 5:
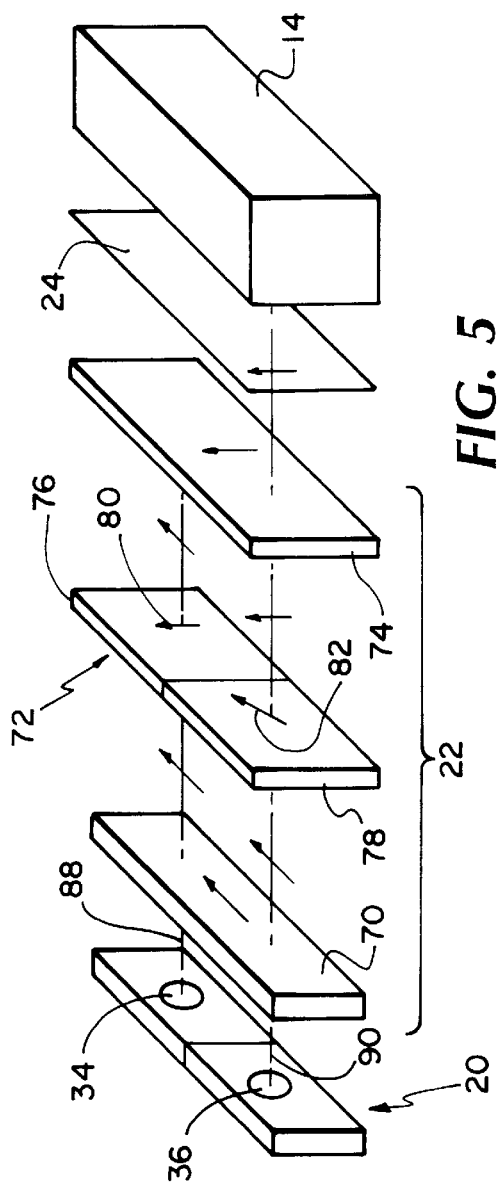
FIGS. 5 and 5A are diagrammatic views of another optical switch for different states of operation.
Figure 5A:
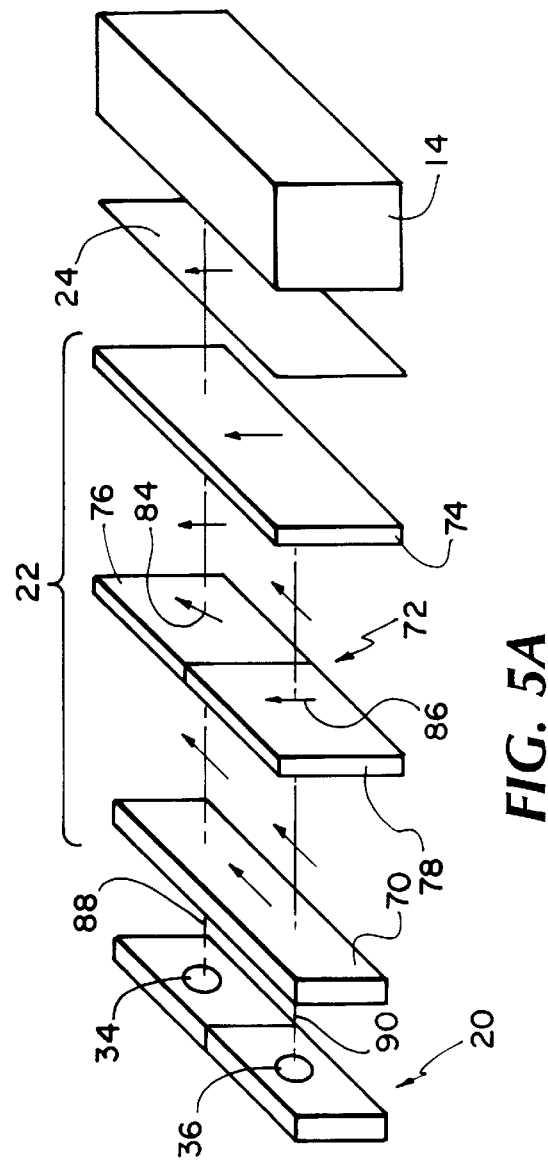

Referring to FIGS. 5 and 5A, in another embodiment, optical switch 22 includes a polarizer 70, a polarization rotator 72, and a polarizer 74. Polarizer 70 and rotator 72 are stacked adjacent to dual aperture plate 20 substantially in the plane of exit pupil 22 of endoscope 12, either distally of aperture plate 20 or proximally of aperture plate 20 as shown. Polarizer 74 can be positioned anywhere in the optical path between rotator 72 and video camera 14, but polarizer 74 is preferably positioned adjacent to rotator 72.

Polarization rotator 72 includes two separate ferroelectric liquid crystals (FLC) 76, 78 which function as broadband switchable half-wave retarders (e.g., Achromatic Rotators available from Displaytech, Inc. of Boulder, Colo., U.S.A.). Rotators 76, 78 are constructed to rotate the polarization of the incoming light by approximately twice the angle the incoming polarization makes with the rotator axis. Rotators 76, 78 alternate between a first state (FIG. 5) with optical axes 80, 82 and a second state (FIG. 5A) with optical axes 84, 86 oriented at angle of 45° with respect to optical axes 80, 82, respectively.

In operation, apertures 34, 36 divide light received from the endoscope into right and left channels 88, 90, and polarizer 70 polarizes right and left channels 88, 90 with a horizontal polarization. In the first state (FIG. 5), the polarization of right optical channel 88 is orthogonal to rotator axis 80; therefore, rotator 76 does not rotate the right channel polarization. The polarization of left channel 90 is oriented at 45° with respect to rotator axis 82; therefore, rotator 78 rotates the left channel polarization by 90° (i.e., to vertical polarization). Polarizer 74 transmits light with vertical polarization (left channel 90) and blocks light with horizontal polarization (right channel 88). Thus, when polarization rotator 72 is in the first state, video camera 14 receives light only from left channel 90.

In the second state (FIG. 5A), the polarization of left optical channel 90 is orthogonal to rotator axis 86; rotator 78 therefore does not rotate the left channel polarization. The polarization of right channel 88 is oriented at 45° with respect to rotator axis 84; rotator 76 therefore rotates the right channel polarization by 90° (i.e., to vertical polarization). Polarizer 74 transmits light with vertical polarization (right channel 88) and blocks light with horizontal polarization (left channel 90). Thus, when polarization rotator 72 is in the second state, video camera 14 receives light only from right channel 88. The embodiment show in FIGS. 5 and 5A provides a high contrast ratio between the right and left optical channels and significantly reduces cross-talk; indeed, because each FLC 76, 78 is in a nonrotating orientation when its respective optical channel is blocked, the contrast ratio between the channels may be as high as 10,000:1.

As mentioned above, the separation of the right and left images is synchronized with the presentation of the images on display 16 by driver 18 (FIG. 1). The EIA Standard RS-170 specifies a vertical video blanking time of 1.25 ms (7.5% of the vertical scanning rate of 60 Hz). The FLC rotators shown in the embodiments of FIGS. 4–5A have switching times on the order of 35–90 μs. Such a high switching speed reduces leakage between the right and left channels, which would otherwise degrade the stereoscopic effect.

The invention provides an improved stereoscopic imaging device for instruments, such as endoscopes, borescopes, and the like. Rapid switching between right and left channels, high contrast ratios between crossed polarizers 70, 74 (FIGS. 5 and 5A) and 52, 54 (FIGS. 4 and 4A), and the use of polymer retarder 50 between parallel polarizers 52, 56 (FIGS. 4 and 4A) advantageously reduce leakage between the right and left channels to provide enhanced stereoscopic visualization. The resulting depth perception enables a user to readily maneuver, for example, an endoscope within a patient's body during a endoscopic procedure, improving the accuracy of the procedure and reducing the overall time needed to complete the procedure.

Still other embodiments are within the scope of the claims. For example, endoscope 12 can be a flexible endoscope. The particular polarizations selected for the right and left channels can be different from that disclosed above, as long as the light in the right and left channels are separable based on the different polarizations of the channels.

Figure 6:
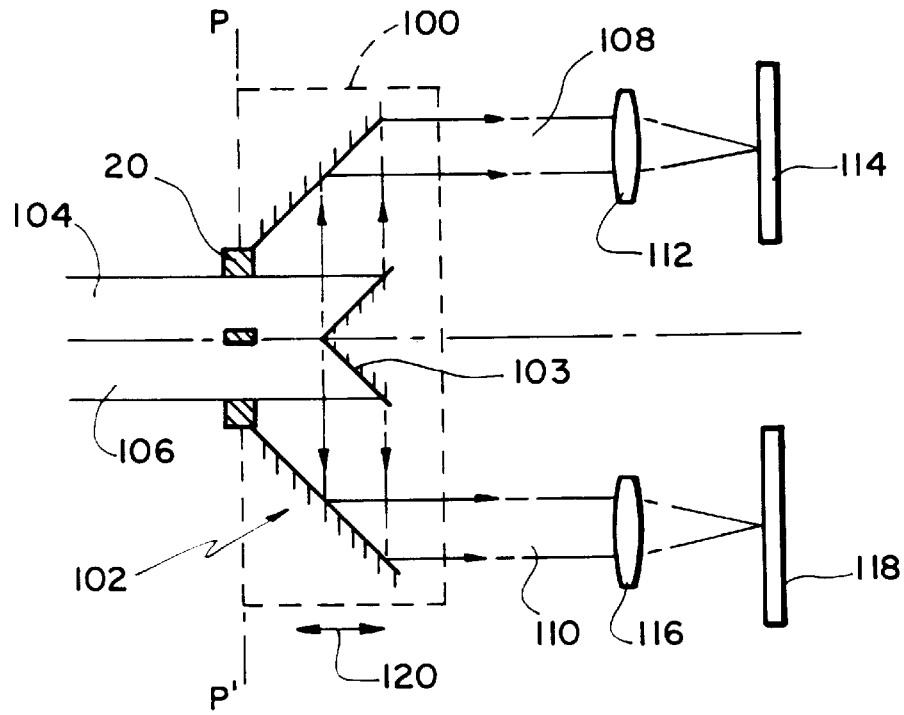
FIG. 6 is a diagrammatic view of a stereoscopic imaging device for use with a dual lens instrument.

FIG. 6 illustrates a stereoscopic imaging device 100 for use with a dual lens instrument (e.g., an endoscope formed from two optical scopes enclosed within a sheath), which transmits light from the distal to the proximal ends of the instrument. Stereoscopic imaging device 100 includes dual aperture plate 20 and delivery optics 102 which includes a mirror system 103 for spatially separating light beams 104, 106 into right and left optical channels 108, 110, respectively. A lens 112 focuses light in right optical channel 108 onto an image sensor 114, and a lens 116 focuses light in left optical channel 110 onto an image sensor 118. As in the above-described embodiments, stereoscopic imaging device 100 is axially movable (as shown by double-headed arrow 120) with respect to the proximal end of the dual lens instrument so that it can be positioned in exit pupil plane P-P'.

Figure 6A:
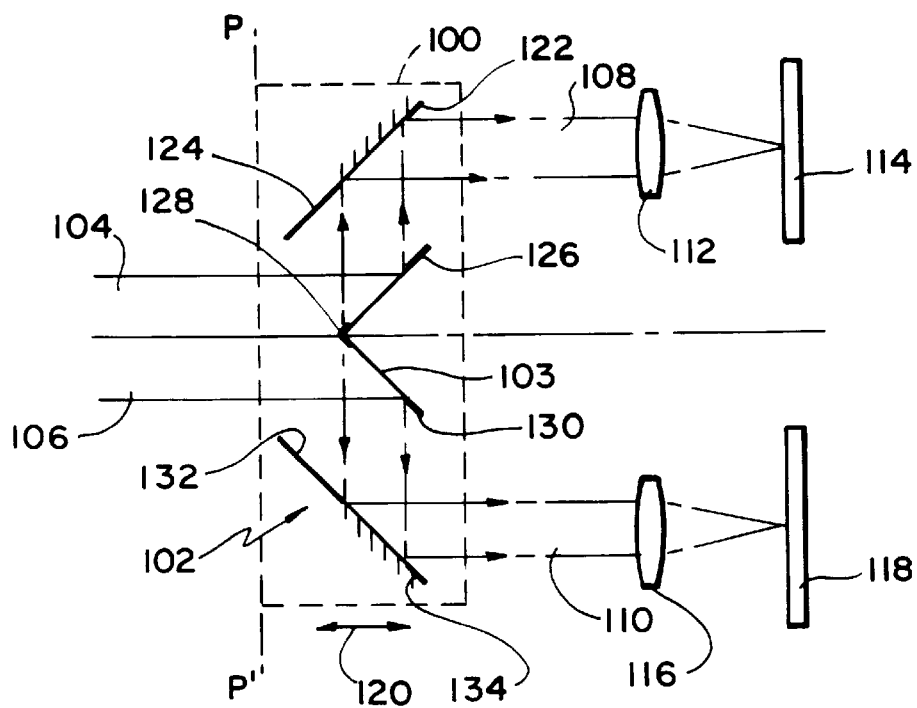
FIG. 6A is a diagrammatic view of another stereoscopic imaging device for use with a dual lens instrument.

Referring to FIG. 6A, in another embodiment, aperture plate 20 is not used; instead, selected portions 122–134 of the mirror surfaces of mirror system 103 are blackened (nonreflecting) so as to define "apertures" for the right and left optical channels.

What is claimed is:

1. A stereoscopic imaging device for attachment to a first and a second instrument, each one of the instruments constructed to transmit light from a distal region of said one of the instruments to a proximal region of said one of the instruments, the imaging device comprising
    a housing constructed to detachably attach to the proximal region of either the first or the second instrument, wherein the first instrument has a first exit pupil located at a first distance from the proximal region of the first instrument, and the second instrument has a second exit pupil located at a second distance from the proximal region of the second instrument, the first distance being different than the second distance,
    a dual aperture plate disposed within the housing and defining right and left, spaced-apart apertures, wherein the dual aperture plate is axially movable to a corresponding one of the first and second distances from the proximal region of one of the instruments when attached to the housing, thereby enabling the right and left apertures to be positioned at symmetric locations substantially in the plane of a corresponding one of the first and second exit pupils, and
    an optical switch disposed within the housing for alternately blocking light received from the attached one of the instruments and passing through the right and left apertures to respectively produce right and left optical channels for generating a stereoscopic view.

2. The imaging device of claim 1 wherein the housing is constructed to attach to the proximal region of an endoscope.

3. The imaging device of claim 1 further comprising an optical device for delivering light from the left and right channels to an imaging sensor for generating a stereoscopic view.

4. The imaging device of claim 1 wherein the housing is constructed to attach to an imaging sensor.

5. The imaging device of claim 1 further comprising a driver for coordinating operation of the optical switch with a display so that a viewer sees the right optical channel with one eye and the left optical channel with the other eye.

6. The imaging device of claim 1 wherein the dual aperture plate is axially movable relative to the housing.

7. A stereoscopic imaging device for attachment to an instrument constructed to transmit light from a distal region of the instrument to a proximal region of the instrument and characterized by an exit pupil located in the vicinity of the proximal region of the instrument, the imaging device comprising
    a housing constructed to attach to the proximal region of the instrument,
    a dual aperture plate disposed within the housing and defining right and left, spaced-apart apertures respectively disposed at symmetric locations substantially in the plane of the exit pupil of the instrument to receive light from the instrument when the housing is attached thereto, and
    an optical switch disposed within the housing for alternately blocking light received from the instrument and passing through the right and left apertures to respectively produce right and left optical channels for generating a stereoscopic view by polarizing the right and left optical channels.

8. A stereoscopic imaging device for attachment to an instrument constructed to transmit light from a distal region of the instrument to a proximal region of the instrument and characterized by an exit pupil located in the vicinity of the Proximal region of the instrument, the imaging device comprising
    a housing constructed to attach to the proximal region of the instrument,
    a dual aperture plate disposed within the housing and defining right and left, spaced-apart apertures respectively disposed at symmetric locations substantially in the plane of the exit pupil of the instrument to receive light from the instrument when the housing is attached thereto, and
    an optical switch including a ferroelectric liquid crystal polarization rotator, the optical switch disposed within the housing for alternately blocking light received from the instrument and passing through the right and left apertures to respectively produce right and left optical channels for generating a stereoscopic view.

9. A stereoscopic imaging device for attachment to an instrument constructed to transmit light from a distal region of the instrument to a proximal region of the instrument and characterized by an exit pupil located in the vicinity of the proximal region of the instrument, the imaging device comprising
    a housing constructed to attach to the proximal region of the instrument,
    a dual aperture plate disposed within the housing and defining right and left, spaced-apart apertures respectively disposed at symmetric locations substantially in the plane of the exit pupil of the instrument to receive light from the instrument when the housing is attached thereto, and an optical switch disposed within the housing for alternately blocking light received from the instrument and passing through the right and left apertures to respectively produce right and left optical channels for generating a stereoscopic view, wherein the optical switch includes a first polarizer for polarizing the right and left optical channels, a second polarizer for permitting light of a selected polarization to pass therethrough, and a polarization rotator disposed between the first and second polarizers for alternately rotating the polarization of the right and left optical channels.

10. The imaging device of claim 9 wherein the first polarizer polarizes the right and left optical channels with orthogonal polarizations, and the polarization rotator is characterized by a first state wherein the right and left optical channels are not rotated by the polarization rotator and by a second state wherein the right and left optical channels are rotated 90° by the polarization rotator.

11. The imaging device of claim 10 wherein the first polarizer comprises two separate polarizers with polarization axes oriented at 90° with respect to each other.

12. The imaging device of claim 10 wherein the optical switch comprises a single ferroelectric liquid crystal polarization rotator.

13. The imaging device of claim 10 wherein the first polarizer is disposed adjacent to the dual aperture plate substantially in the plane of the exit pupil of the instrument when the housing is attached thereto.

14. The imaging device of claim 10 further comprising an optical retarder coupled to the housing and disposed between the polarization rotator and the second polarizer for adjusting contrast ratios of the right and left optical channels.

15. The imaging device of claim 9 wherein the first polarizer polarizes the right and left optical channels with the same polarization, and the polarization rotator is characterized by a first state wherein the right optical channel is not rotated by the polarization rotator and the left optical channel is rotated 90° by the polarization rotator, and by a second state wherein the right optical channel is rotated by 90° by the polarization rotator and the left optical channel is not rotated by the polarization rotator.

16. The imaging device of claim 15 wherein the optical switch comprises two separate ferroelectric liquid crystal polarization rotators with optical axes oriented at 45° with respect to each other.

17. The imaging device of claim 15 wherein the first polarizer and the polarization rotator are disposed adjacent to the dual aperture plate substantially in the plane of the exit pupil of the instrument when the housing is attached thereto.

18. A stereoscopic imaging device for attachment to an instrument constructed to transmit light from a distal region of the instrument to a proximal region of the instrument and characterized by an exit pupil located in the vicinity of the proximal region of the instrument, the imaging device comprising
a housing constructed to detachably attach to the proximal region of the instrument,
a dual aperture plate disposed within the housing and defining right and left, spaced-apart apertures respectively disposed at symmetric locations substantially in the plane of the exit pupil of the instrument to receive light from the instrument when the housing is attached thereto, the dual aperture plate being axially movable relative to said housing and to the proximal region of the instrument when the housing is coupled thereto, and
an optical switch disposed within the housing for alternately blocking light received from the instrument and passing through the right and left apertures to respectively produce right and left optical channels for generating a stereoscopic view.

19. A stereoscopic imaging device for attachment to an instrument constructed to transmit light from a distal region of the instrument to a proximal region of the instrument and characterized by an exit pupil located in the vicinity of the proximal region of the instrument, the imaging device comprising
a housing constructed to attach to the proximal region of the instrument,
a dual aperture plate disposed within the housing and defining right and left, spaced-apart apertures respectively disposed at symmetric locations substantially in the plane of the exit pupil of the instrument to receive light from the instrument when the housing is attached thereto, the right and left apertures of the dual aperture plate being symmetrically spaced from a common axis, and the right and left apertures are elongated along a respective dimension parallel to the common axis, and
an optical switch disposed within the housing for alternately blocking light received from the instrument and passing through the right and left apertures to respectively produce right and left optical channels for generating a stereoscopic view.

20. The imaging device of claim 19 wherein the right and left apertures are generally elliptical in shape.

21. A stereoscopic imaging device for attachment to an endoscope constructed to be inserted into a patient's body to transmit light from a region inside the patient's body to a proximal region of the endoscope and characterized by an exit pupil located in the vicinity of the proximal region of the endoscope, the imaging device comprising
a housing constructed to attach to the proximal region of the endoscope,
a dual aperture plate disposed within the housing and defining right and left, spaced-apart apertures respectively disposed at symmetric locations substantially in the plane of the exit pupil of the endoscope to receive light from the endoscope when the housing is attached thereto,
a first polarizer for polarizing the right and left optical channels,
a second polarizer for permitting light of a selected polarization to pass therethrough, and
a ferroelectric liquid crystal polarization rotator disposed within the housing between the first and second polarizers for alternately blocking light received from the endoscope and passing through the right and left apertures to respectively produce right and left optical channels for generating a stereoscopic view of the region inside the patient's body.

22. A stereoscopic imaging system for attachment a first and a second instrument, each one of the instruments constructed to transmit light from a distal region of said one of the instruments to a proximal region of said one of the instruments, the imaging device comprising
a housing constructed to detachably attach to the proximal region of either the first or the second instrument, wherein the first instrument has a first exit pupil located at a first distance from the proximal region of the first instrument, and the second instrument has a second exit pupil located at a second distance from the proximal region of the second instrument, the first distance being different than the second distance,
a dual aperture plate disposed within the housing and defining right and left, spaced-apart apertures, wherein the dual aperture plate is axially movable to a corresponding one of the first and second distances from the proximal region of one of the instruments when attached to the housing, thereby enabling the right and left apertures to be positioned at symmetric locations substantially in the plane of a corresponding one of the first and second exit pupils, an optical switch disposed within the housing for alternately blocking light received from the attached one of the instruments and passing through the right and left apertures to respectively produce right and left optical channels for generating a stereoscopic view, and an imaging sensor coupled to the housing for generating a stereoscopic view.

23. The imaging device of claim 22 wherein the dual aperture plate is axially movable relative to the housing.

24. A stereoscopic imaging system for attachment to an instrument constructed to transmit light from a distal region of the instrument to a proximal region of the instrument and characterized by an exit pupil located in the vicinity of the proximal region of the instrument, the imaging device comprising a housing constructed to attach to the proximal region of the instrument, a dual aperture plate disposed within the housing and defining right and left, spaced-apart apertures respectively disposed at symmetric locations substantially in the plane of the exit pupil of the instrument to receive light from the instrument when the housing is attached thereto, an optical switch, comprising a ferroelectric liquid crystal polarization rotator and disposed within the housing for alternately blocking light received from the instrument and passing through the right and left apertures to respectively produce right and left optical channels for generating a stereoscopic view, and an imaging sensor coupled to the housing for generating a stereoscopic view.

25. The imaging device of claim 24 wherein the optical switch further comprises a first polarizer for polarizing the right and left optical channels, and a second polarizer for permitting light of a selected polarization to pass therethrough, the ferroelectric liquid crystal polarization rotator being disposed between the first and second polarizers for alternately rotating the polarization of the right and left optical channels.

26. A stereoscopic imaging system comprising a first and a second endoscope, each one of the endoscopes constructed to be inserted into a patient's body to transmit light from a region inside the patient's body to a proximal region of said one of the endoscopes, the first endoscope having a first exit pupil located at a first distance from the proximal region of the first endoscope, the second endoscope having a second exit pupil located a second distance from the proximal region of the second endoscope, the first distance being different than the second distance, a housing constructed to attach to the proximal region of either the first or the second endoscope, a dual aperture plate disposed within the housing and defining right and left, spaced-apart apertures, wherein the dual aperture plate is axially movable to a corresponding one of the first and second distances from the proximal region of one of the endoscopes when attached to the housing, thereby enabling the right and left apertures to be positioned at symmetric locations substantially in the plane of a corresponding one of the first and second exit pupils, an optical switch disposed within the housing for alternately blocking light received from the attached one of the endoscopes and passing through the right and left apertures to respectively produce right and left optical channels for generating a stereoscopic view of the region inside the patient's body, and an imaging sensor coupled to the housing for generating a stereoscopic image of the region inside the patient's body based on the right and left optical channels produced by the optical switch.

27. The imaging device of claim 26 wherein the dual aperture plate is axially movable relative to the housing.

28. A stereoscopic imaging system comprising an endoscope constructed to be inserted into a patient's body to transmit light from a region inside the patient's body to a proximal region of the endoscope and characterized by an exit pupil located in the vicinity of the proximal region of the endoscope, a housing constructed to attach to the proximal region of the endoscope, a dual aperture plate disposed within the housing and defining right and left, spaced-apart apertures respectively disposed at symmetric locations substantially in the plane of the exit pupil of the instrument to receive light from the endoscope when the housing is attached thereto, an optical switch, comprising a ferroelectric liquid crystal polarization rotator and disposed within the housing for alternately blocking light received from the instrument and passing through the right and left apertures to respectively produce right and left optical channels for generating a stereoscopic view of the region inside the patient's body, and an imaging sensor coupled to the housing for generating a stereoscopic image of the region inside the patient's body based on the right and left optical channels produced by the optical switch.

29. The imaging device of claim 28 wherein the optical switch further comprises a first polarizer for polarizing the right and left optical channels, and a second polarizer for permitting light of a selected polarization to pass therethrough, the ferroelectric liquid crystal polarization rotator being disposed between the first and second polarizers for alternately rotating the polarization of the right and left optical channels.

30. A method for generating a stereoscopic image from light received from a first or a second instrument, each one the instruments being constructed to transmit light from a distal region of said one of the instruments to a proximal region of said one of the instruments, the method comprising the steps of receiving light from the proximal region of said one of the instruments, the proximal region attached to a housing constructed to detachably attach to the proximal region of either the first or the second instrument, wherein the first instrument has a first exit pupil located at a first distance from the proximal region of the first instrument, and the second instrument has a second exit pupil located at a second distance from the proximal region of the second instrument, the first distance being different than the second distance, providing a dual aperture plate defining right and left, spaced-apart apertures, defining right and left optical channels, axially moving the dual aperture plate to a corresponding one the first and second distances from the proximal region of one of the instruments when attached to the housing, thereby positioning the right and left apertures at symmetric locations substantially in the plane of a corresponding one of the first and second exit pupils, and alternately blocking the right and left optical channels for generating a stereoscopic view.

31. A method for generating a stereoscopic image from light received from an instrument that is constructed to transmit light from a distal region of the instrument to a proximal region of the instrument and is characterized by an exit pupil in the vicinity of a proximal region of the instrument, the method comprising the steps of receiving light from the proximal region of the instrument, and at symmetric locations substantially in the plane of the exit pupil of the instrument, defining right and left optical channels, causing the right and left optical channels to have different polarizations, and alternately blocking the right and left optical channels for generating a stereoscopic view.

32. The method of claim 31 wherein the right and left optical channels are alternately blocked based on the different polarizations of the right and left optical channels.

33. A method for generating a stereoscopic image from light received from an instrument that is constructed to transmit light from a distal region of the instrument to a proximal region of the instrument and is characterized by an exit pupil in the vicinity of a proximal region of the instrument, the method comprising the steps of receiving light from the Proximal region of the instrument, and at symmetric locations substantially in the plane of the exit pupil of the instrument, defining right and left optical channels using a dual aperture plate, adjusting an axial position of the dual aperture plate until the dual aperture plate is located substantially in a plane of the exit pupil of the instrument, and alternately blocking the right and left optical channels for generating a stereoscopic view.

* * * * *